US008715157B2

(12) United States Patent  
Berg et al.

(10) Patent No.: US 8,715,157 B2
(45) Date of Patent: May 6, 2014

(54) MAGNETIC GASTRIC BAND OR THE LIKE, AND RELATED METHODS

(75) Inventors: Todd A. Berg, Stillwater, MN (US); Steven D. Kruse, St. Michael, MN (US); Jerome K. Grudem, Jr., Rogers, MN (US); Jon St. Germain, Elk River, MN (US); Eric Stainbrook, St. Paul, MN (US)

(73) Assignee: Torax Medical, Inc., Shoreview, MN (US)

(*) Notice: Subject to any disclaimer, the term of this patent is extended or adjusted under 35 U.S.C. 154(b) by 1126 days.

(21) Appl. No.: 12/229,343

(22) Filed: Aug. 22, 2008

(65) Prior Publication Data

US 2009/0062824 A1    Mar. 5, 2009

Related U.S. Application Data

(60) Provisional application No. 60/966,406, filed on Aug. 27, 2007.

(51) Int. Cl.
  *A61F 2/00* (2006.01)
  *A61F 5/00* (2006.01)

(52) U.S. Cl.
  CPC .............. *A61F 5/005* (2013.01); *A61F 2/0018* (2013.01); *A61F 5/0066* (2013.01)
  USPC .......................................... 600/37; 623/14.13

(58) Field of Classification Search
  CPC ....... A61F 2/0018; A61F 2/0009; A61F 2/02; A61F 2210/009; A61F 2250/001; A61F 2250/0045; A61F 5/005; A61F 5/0063; A61F 5/0066
  USPC .......................... 600/28–32, 37; 606/151–157; 623/23.64, 14.13; 128/897–899
  See application file for complete search history.

(56) References Cited

U.S. PATENT DOCUMENTS 5,002,563 A * 3/1991 Pyka et al. .................... 606/222
5,569,199 A * 10/1996 Solar .......................... 604/103.1

(Continued)

FOREIGN PATENT DOCUMENTS

DE        30 11 742        10/1981
EP         1 676 543        7/2006
WO    WO 2006/020382       2/2006

OTHER PUBLICATIONS

G. Moragas et al., "Relations Among Intragastric Pressure, Postcibal Perception, and Gastric Emptying," the American Physiological Society, pp. G1112-G1117, 1993.

(Continued)

*Primary Examiner* — Charles A Marmor, II
*Assistant Examiner* — Carrie R Dorna
(74) *Attorney, Agent, or Firm* — Ropes & Gray LLP; Jeffrey H. Ingerman

(57) ABSTRACT

A structure that can be used as a gastric band (and that may also have other uses as an implant elsewhere in a patient) includes a plurality of magnetic elements in a serial array that can be implanted so that the array extends in a circumferential direction around the patient's stomach (or other body tissue structure in the patient). Circumferentially adjacent magnetic elements magnetically attract one another to apply radial pressure to the tissue structure encompassed by the array, but those elements can also move apart in response to sufficient outward pressure from the encompassed tissue structure and/or the contents of (e.g., food in) that tissue structure. When used as a gastric band, the device can provide resistance to excessive food intake, which can help promote weight loss.

6 Claims, 13 Drawing Sheets

(56) References Cited

U.S. PATENT DOCUMENTS

| | | | |
|---|---|---|---|
| 5,771,903 A * | 6/1998 | Jakobsson | 128/898 |
| 6,916,326 B2 | 7/2005 | Benchetrit | |
| 7,121,283 B2 | 10/2006 | Stack et al. | |
| 7,175,589 B2 | 2/2007 | Deem et al. | |
| 7,326,172 B2 | 2/2008 | Miller | |
| 7,468,060 B2 | 12/2008 | Utley et al. | |
| 2004/0147801 A1 | 7/2004 | Kugler et al. | |
| 2004/0260316 A1 * | 12/2004 | Knudson et al. | 606/151 |
| 2005/0283235 A1 * | 12/2005 | Kugler et al. | 623/14.13 |
| 2007/0213751 A1 | 9/2007 | Scirica et al. | |
| 2007/0250020 A1 * | 10/2007 | Kim et al. | 604/264 |
| 2009/0125102 A1 | 5/2009 | Cartledge et al. | |
| 2010/0179376 A1 | 7/2010 | Kassab et al. | |

OTHER PUBLICATIONS

N.K. Ahluwalia et al., "Relaxation Responses of the Human Proximal Stomach to Distension During Fasting and After Food," the American Physiological Society, pp. G166-G171, 1994.

P. Rossi et al., "Stomach Distension Increases Efferent Muscle Sympathetic Nerve Activity and Blood Pressure in Healthy Humans," Journal of the Neurological Sciences 161 (1998) 148-155.

M. Belachew et al., "History of Lap-Band®: From Dream to Reality," Obesity Surgery, 11, 2001, 297-302.

* cited by examiner

MAGNETIC GASTRIC BAND OR THE LIKE, AND RELATED METHODS

This application claims the benefit of U.S. provisional patent application 60/966,406, filed Aug. 27, 2007, which is hereby incorporated by reference herein in its entirety.

BACKGROUND OF THE INVENTION

This invention relates to medical implants to be implanted around a patient's tissue structure, body conduit, or organ. An illustrative use of the invention is implanting one or more of such implants around a patient's stomach to treat obesity.

Surgical intervention for the treatment of obesity is already in practice. Patients with a body mass index (BMI) greater than 40, or a BMI greater than 35 but with one or more co-morbid conditions are currently candidates for surgical intervention. In addition, there is ongoing research related to patients with lower BMI (e.g., 30-35) to determine the risk/benefit of using these therapies in such patients. In general, as the BMI threshold is lowered, the therapy risk profile must be reduced because this patient population has less benefit to gain. Gastric bypass and gastric banding are the two most common procedures performed.

Conventional gastric banding involves the placement of a rigid ring (often with an inflatable member on the inner surface of the ring) around the outside of the stomach to create a small conduit or stoma between the proximal and distal stomach. This restriction serves to slow the rate of food passage through the stomach, increasing the patient's feeling of fullness, thereby reducing food intake and resulting in the patient losing weight. The inflatable member (if included) allows the stoma to be adjusted smaller or larger in diameter by adding volume to or subtracting volume from the inflatable member in response to inadequate weight loss, stoma obstruction, patient symptoms and tolerance, etc. The adjustment is often accomplished through a fluid-filled reservoir and port, which are implanted in the patient's abdomen. One common way a physician can add or remove fluid is by accessing a port beneath the patient's skin, e.g., by injection with a syringe. In another method, the stoma adjustment is accomplished through an expansion of a polymer material, which is activated by mechanical means to increase or decrease the extent of the restriction. In either case, adjustments are made based on caregiver interaction and are in response to balancing the need to accelerate/maintain weight loss in relation to patient discomfort.

In general, known gastric banding techniques are reasonably effective in causing weight loss. The known technologies are, however, subject to certain drawbacks. One drawback is that implantation of a fluid reservoir can be associated with infection. Another possible drawback is that adjustments performed by injection with a syringe can lead to punctures of the port and/or tubing, causing loss of the contained fluid and rendering the treatment ineffective. Additionally, gradual loss of pressure due to osmosis of fluid from the inflatable member can necessitate regular interventions to adjust the diameter of the ring (gastric band).

Another possible drawback of conventional gastric banding is due to the nature of its fixed stoma or constriction. It has been noted that patients who consume their food by drinking high calorie sweets, liquids, or soft foods do not benefit substantially from treatment with a gastric band. Furthermore, patients are encouraged not to drink liquids with food because this has been shown to speed up digestion and passage through the stoma, which can limit the effectiveness of gastric banding.

SUMMARY OF THE INVENTION

The present invention aims to address the above and other possible drawbacks of conventional gastric banding techniques. Certain aspects of the invention may also have other applications, so the invention is not wholly confined to gastric banding. But gastric banding will be mentioned most frequently herein and it serves as a useful context in which to illustrate the invention. (Examples of other contexts in which at least some aspects of the present invention may be applied are shown and/or described in such references as Deem et al. U.S. Pat. No. 7,175,589 and Kugler et al. WIPO publication WO 2006/020382.)

In accordance with certain possible aspects of the invention, implantation of an annular array of structures that are attractive to one another (e.g., magnetically) can be used to create a pressure-mediated valve between a proximal stomach pouch and the more distal stomach. The passage of food of any consistency can be held in the proximal stomach until a certain pressure is attained. When adequate pressure is attained, the implanted structures begin to separate from one another and allow food to pass from the proximal stomach pouch, thereby reducing pressure in the pouch. In this way, pressure, and therefore a feeling of fullness, is maximally maintained, thereby promoting weight loss.

The implants of this invention preferably contain no fluids and include no fluid reservoirs. They therefore have none of the above-mentioned drawbacks of implants that do rely on such expedients. The implants of this invention, by nature of their design, automatically respond to a physiological parameter (e.g., gastric pressure), which drives multiple mechanisms in the body that influence weight control.

Barostat studies have found that different patients experience feelings of fullness and discomfort at different pressures between 10-25 mm Hg. In contrast to adjusting the diameter of the restriction provided by a gastric band implant, it may be preferable to first understand the tolerance of a patient to gastric pressure, and then implant a pressure-sensitive valve in accordance with this invention that coincides with that patient's feeling of fullness and/or discomfort. This can create a more effective weight loss therapy that is less dependent on patient compliance with a specific diet or eating pattern.

More generally, the invention may comprise a pressure-mediated device placed around a patient's tissue structure, body organ, or body lumen to control the rate of fluid, solid, or other content passage through the tissue structure. The tissue structure may be, for example, the esophagus, stomach, duodenum, rectum or other tissue structure. The device is movable between at least two states in response to the pressure within the tissue structure. The device may control more than one rate of passage through the tissue structure. The device is preferably self-regulating between the flow rates in response to the pressure within the tissue structure. In the case of gastric banding, for example, the compliance (variability) of the device's diametrical displacement may be altered and refined in a number of ways described herein to optimize the balance of weight loss and patient discomfort.

Further features of the invention, its nature and various advantages will be more apparent from the accompanying drawings and the following detailed description.

BRIEF DESCRIPTION OF THE DRAWINGS

FIGS. 4a and 4b are sometimes referred to collectively as FIG. 4.

DETAILED DESCRIPTION

Figure 4A:
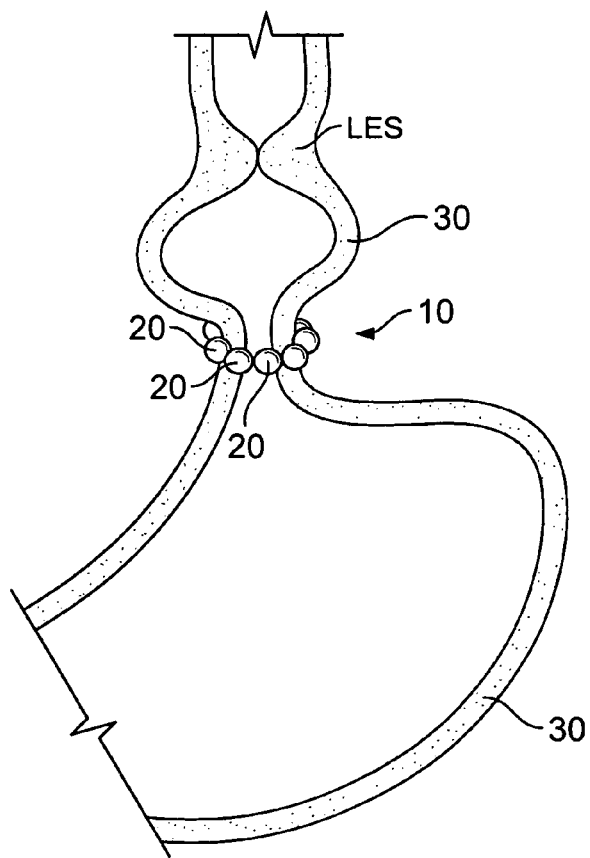
FIG. 4a is a simplified view, partly in section, showing the FIG. 3 anatomy with illustrative modification in accordance with the invention.
Figure 4B:
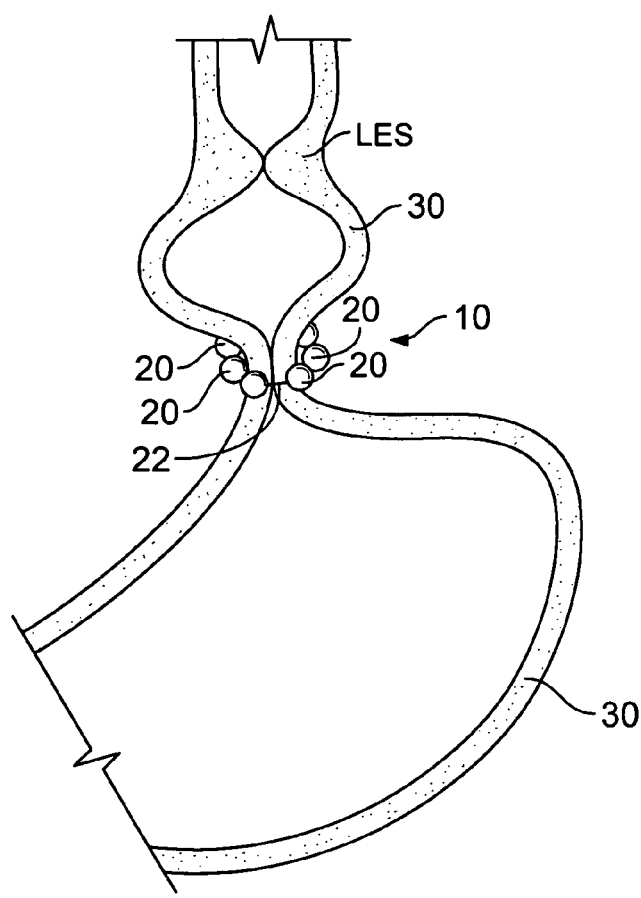
FIG. 4b is similar to FIG. 4a for another illustrative embodiment in accordance with the invention.

In one embodiment (illustrated, for example, by FIG. 4), a device 10 in accordance with the invention includes a series of structures 20 which attract one another, e.g., by magnetic attraction. Examples of how device 10 may be constructed are shown in Deem et al. U.S. Pat. No. 7,175,589 and Kugler et al. WIPO publication WO 2006/020382. Structures 20 are disposed in a generally circular array around the tissue structure (e.g., a patient's stomach 30 in FIG. 4), and the attraction between circumferentially adjacent ones of structures 20 acts to squeeze or reduce the diameter of the encompassed tissue structure. The attraction may serve to partially or fully close the encompassed tissue structure to substantially prevent the passage of fluid or solid material while the pressure of the material wanting to pass is below a prescribed threshold. In one case (e.g., as shown in FIG. 4b), when device 10 has squeezed tissue structure 30 down to a stoma of approximately zero lumen diameter, device 10 may exert a small residual pressure on the tissue, but it does not exert excessive tissue-pinching pressure on tissue 30, which could cause necrosis of the tissue. (In other words, FIG. 4b shows partially open beads 20 with a closed stoma.) In another case (e.g., as shown in FIG. 4a), a non-zero minimum area is encompassed by device 10 when all of attracted structures 20 are in circumferentially adjacent contact with each other and the pressure within tissue structure 30 is below a prescribed threshold. (In other words, FIG. 4a shows closed beads 20 with an open stoma.) In this state, the encompassed tissue structure is held to a predetermined diameter and device 10 does not act to squeeze the tissue further.

In response to an increase in pressure in tissue structure 30 above a prescribed threshold, one or more circumferentially adjacent structures 20 move away from one another in the circumferential direction around the tissue structure. This results in a second state of device 10. Although structures 20 can thus move away from one another, links 22 between circumferentially adjacent ones of structures 20 always keep structures 20 in a circumferential array around tissue 30. (See later FIGS. for illustrative, more detailed depictions of links 22.) In addition, each link 22 may limit the maximum distance that the structures 20 joined by that link can move apart.

The above-mentioned second state of device 10 may hold encompassed tissue structure 30 to a second predetermined diameter, which is larger than the earlier-mentioned tissue structure diameter. With tissue structure 30 having this second diameter, a second (greater) rate of material (food) passage through the tissue structure can occur. A decrease in pressure in tissue structure 30 below the above-mentioned prescribed threshold results in device 10 moving back to the first state and rate of passage. It should be noted that the number of states (circumferential sizes) that device 10 is capable of may be two or more, up to a possibly very large number of different circumferential size states, with each state being associated with a prescribed pressure within tissue structure 30. For example, the resistance to opening from one state to the next may vary from state to state based on different strengths of different magnets (e.g., relatively weak first stage magnets separate relatively easily, but stronger second stage magnets do not separate as easily). It may also be desirable to construct different devices 10 with different strengths for use in different patients or for use at different locations within a patient. For example, not all patients may benefit from devices 10 of the same strength.

As one possible example of some of the principles discussed above, FIG. 2 illustrates some aspects of possible operation of a two-state device 10. In this embodiment, device 10 may be placed around the stomach 30 to control the rate of passage of food from the fundus to the body (corpus) of the stomach. (See FIG. 3 for a simplified depiction of typical patient anatomy prior to modification in accordance with the invention. The esophagus, lower esophageal sphincter (LES) and stomach 30 (including the fundus, body (corpus), and antrum) are shown. Modification of this anatomy by device 10 in accordance with the invention is shown in FIG. 4.)

Figure 2:
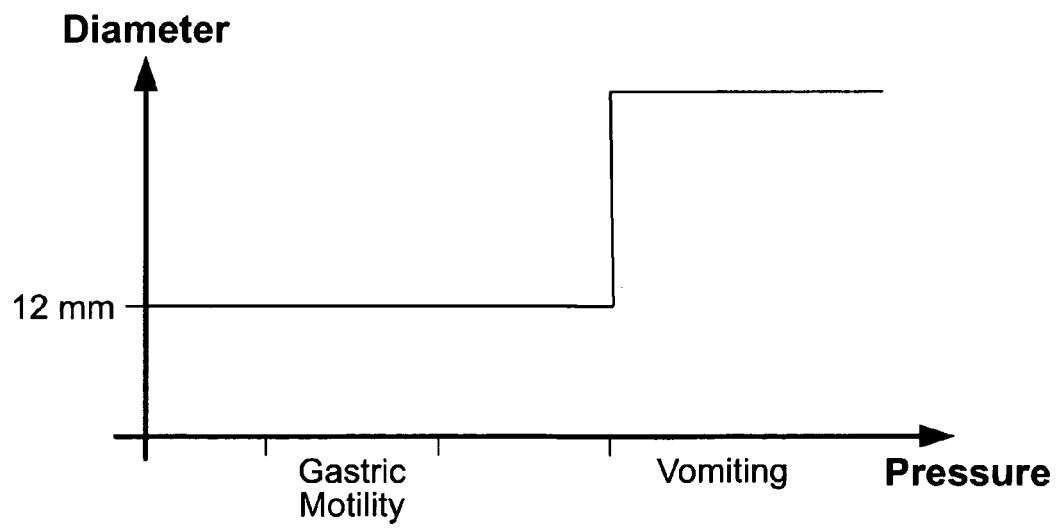
FIG. 2 is a simplified graph showing operation of another illustrative embodiment of apparatus in accordance with the invention.
Figure 3:
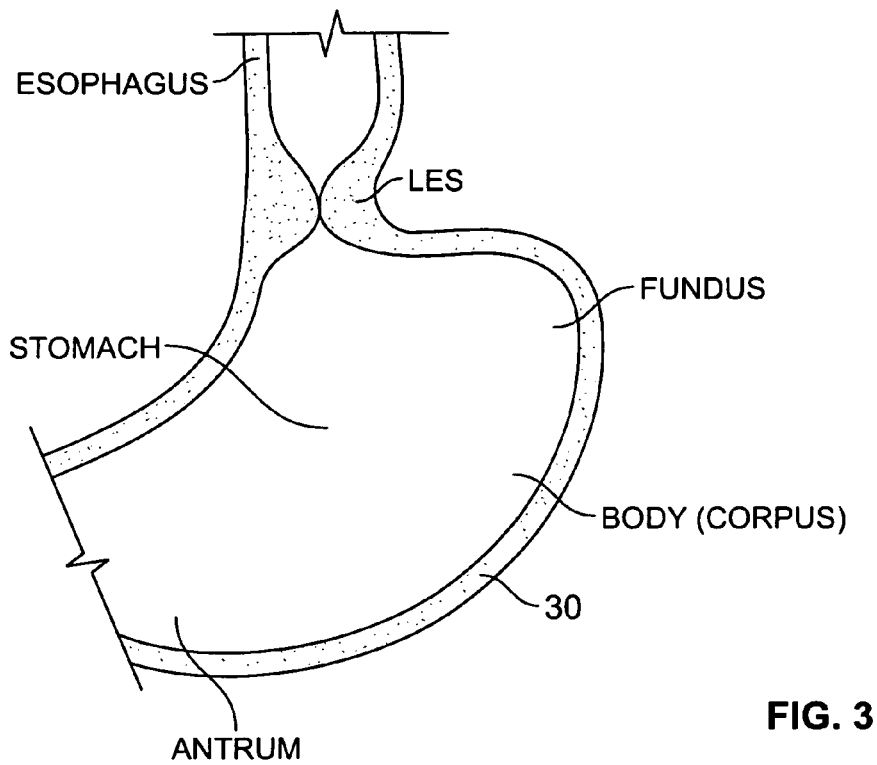
FIG. 3 is a simplified sectional view of a portion of a typical patient's internal anatomy.

One state of the two-state device 10 currently being described may be shown toward the left in FIG. 2. In this state, the device may create a stoma (e.g., of 12 mm maximum diameter) and limit the rate of passage of food for pressures within the normal range of gastric motility. This may be desirable to reduce food intake in cases of morbid obesity, where device 10 holds a fixed diameter and a maximum fixed rate of food passage within the normal gastric motility pressure range. Device 10 may self-regulate to a larger diameter (shown toward the right in FIG. 2) and consequently a larger flow rate in cases where intra-gastric pressure exceeds the upper threshold of gastric motility (i.e., when vomiting) to allow rapid expulsion of stomach contents.

Figure 1:
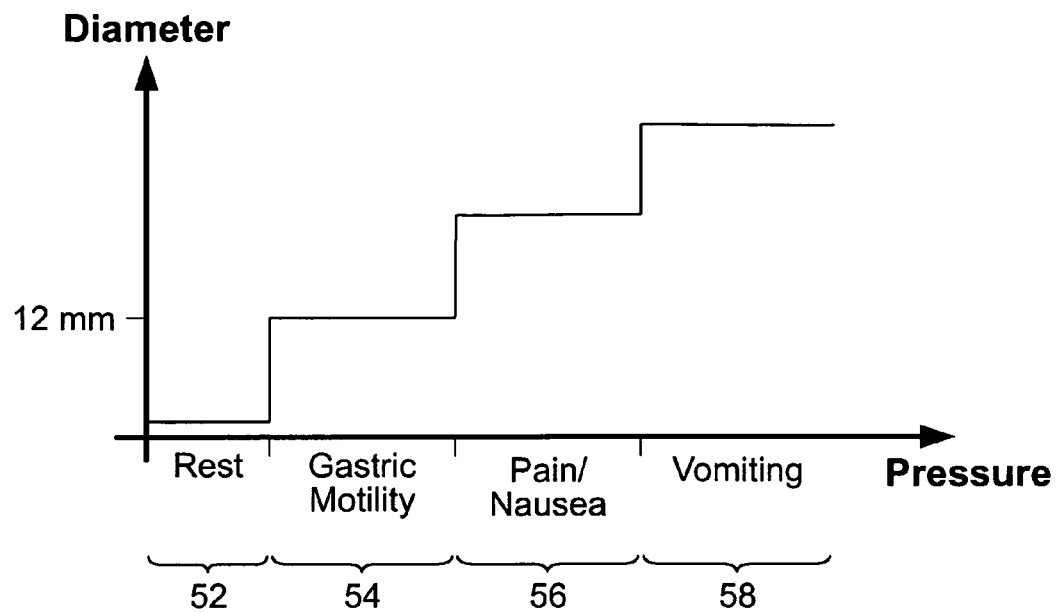
FIG. 1 is a simplified graph showing operation of an illustrative embodiment of apparatus in accordance with the invention.

As another possible example of some of the principles discussed above, FIG. 1 shows a device that is designed to have four possible states (circumferential sizes). For example, this device 10 may have a resting state 52 corresponding to an empty stomach. In this state each magnetic element 20 in device 10 is in contact with the circumferentially adjacent magnetic elements, and device 10 accordingly has its smallest circumferential size around tissue 30. FIG. 1 shows this size being less than 12 mm, but the area encompassed by device 10 is still greater than zero as discussed earlier in this specification. A second state 54 of the device 10 operationally illustrated by FIG. 1 corresponds to the pressure range of gastric motility. In this state some number of circumferentially adjacent magnetic elements 20 are separated from one another. FIG. 1 shows device 10 encompassing an area of about 12 mm diameter in second state 54. A third state 56 of the device 10 operationally illustrated by FIG. 1 corresponds to the fundus pressure range where sensations of discomfort and nausea persist. In this state a greater number of circumferentially adjacent magnetic elements 20 are separated from one another than in state 54. FIG. 1 shows device 10 encompassing an area greater than 12 mm diameter in third state 56. A fourth state 58 of the device 10 operationally illustrated by FIG. 1 corresponds to intragastric pressures that induce vomiting. In this state a maximum number of circumferentially adjacent magnetic elements 20 are separated from one another and the circumferential size of device 10 is accordingly even greater than in third state 56.

It will be appreciated that the examples shown in FIGS. 1 and 2 are not restrictive or exhaustive.

Figure 7:
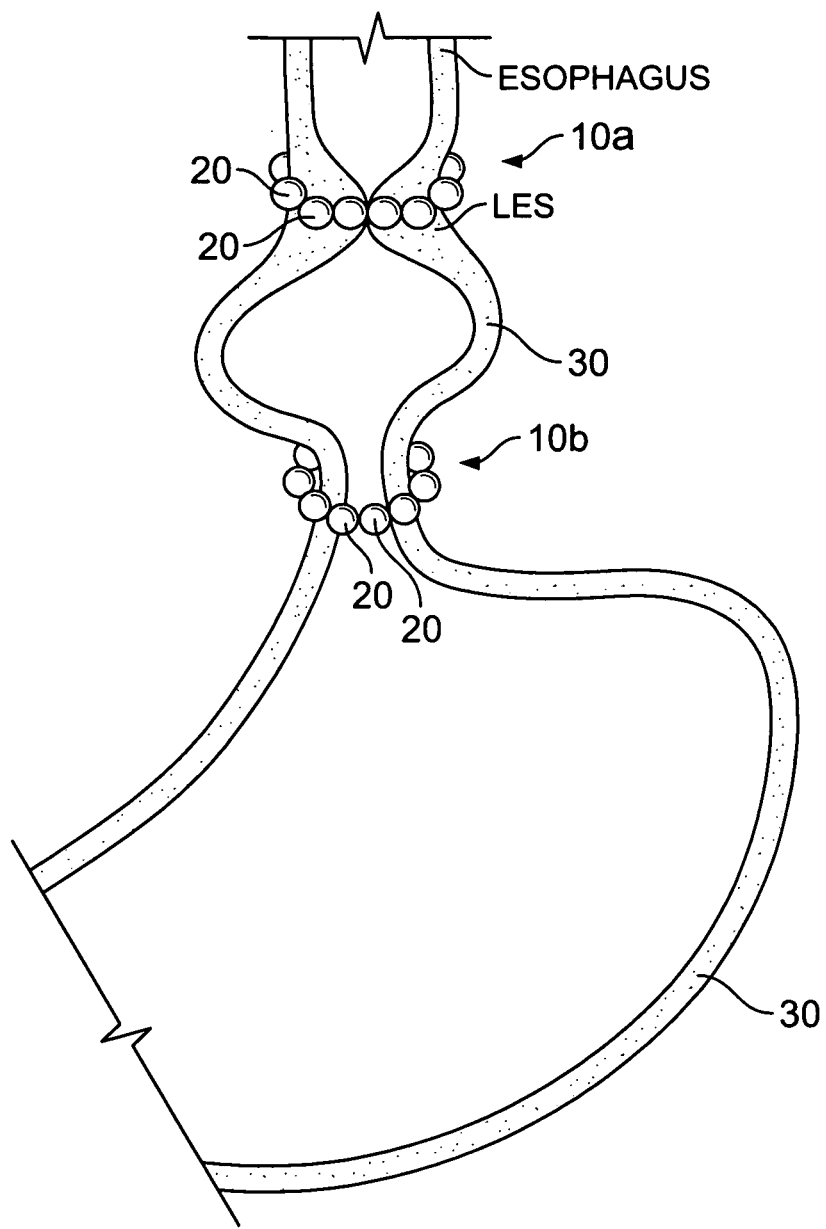
FIG. 7 is another view similar to FIG. 4 showing another illustrative embodiment of the invention.

In other embodiments (illustrated by FIGS. 7 and 8), two or more devices 10a/10b may be placed on a tissue structure (or adjoining tissue structures,) to control the inlet and outlet rate of flow through the tissue structure(s). As shown in FIG. 7, for example, device 10b may be placed around the stomach 30 in the region of the fundus to control the rate of food passage from the fundus or proximal portion of the stomach to the distal or antral portion of the stomach. Such placement of device 10b segregates the stomach into two distinct areas: the main body of the stomach, and a proximal pouch. Device 10b controls the rate of outlet flow distal to the pouch.

In the illustrative embodiment shown in FIG. 7, a second device 10a is placed proximal to the first device 10b. For example, device 10a may be placed around the lower esophageal sphincter (LES) to control the rate of inlet into the above-mentioned stomach pouch or to prevent reflux of the pouch contents back into the esophagus.

In the illustrative embodiment shown in FIG. 7, both devices 10a and 10b serve as pressure check valves, which control a maximum flow rate into and out of the above-mentioned stomach pouch within a given pressure range, and which self-regulate to at least a second state in response to pressure changes proximal to, within, or distal to the above-mentioned pouch (i.e., the portion of the stomach between devices 10a and 10b).

Figure 8:
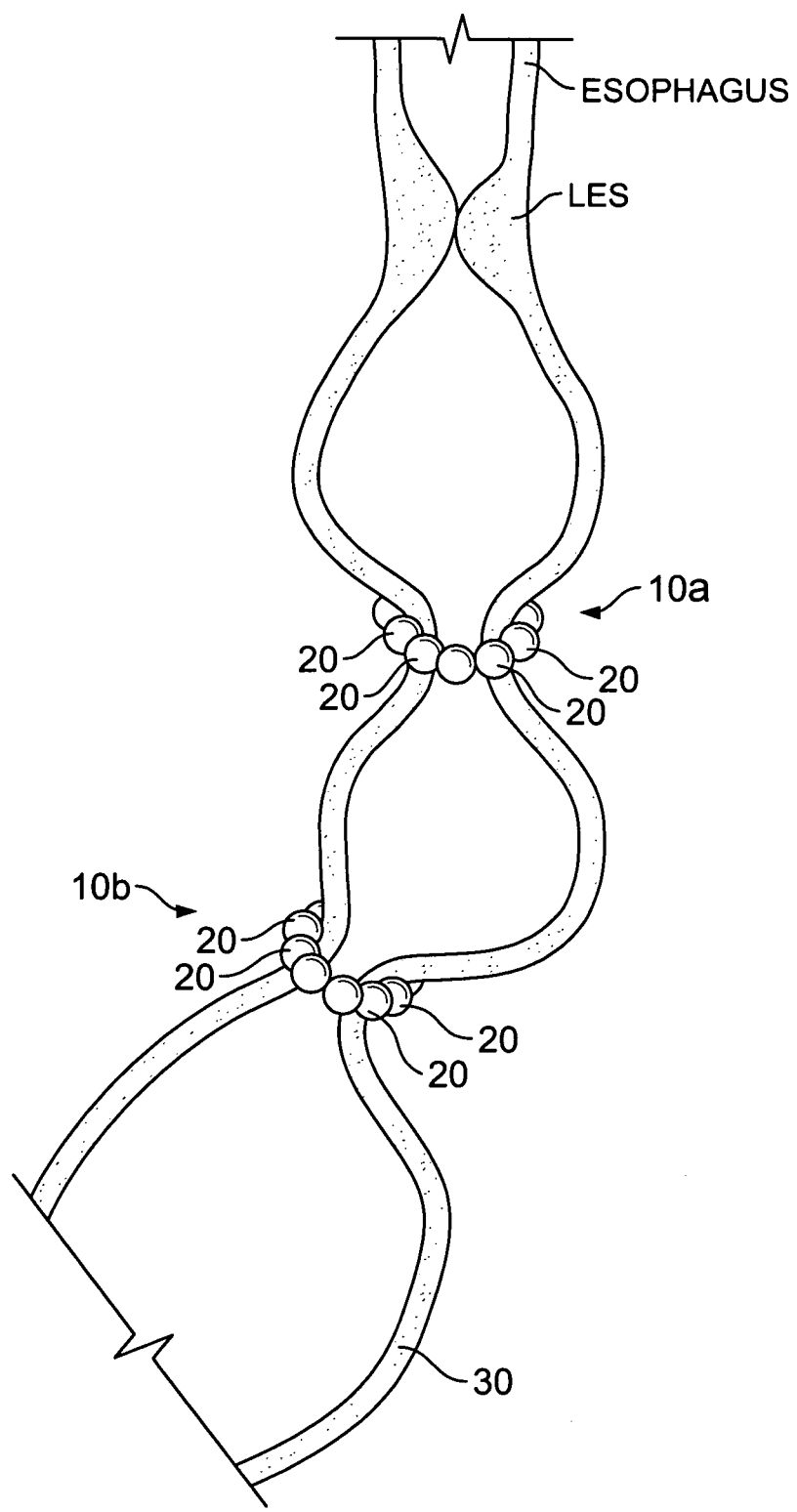
FIG. 8 is another view similar to FIG. 7 showing still another illustrative embodiment of the invention.

FIG. 8 shows another example in which device 10a may be placed approximately where device 10b is placed in FIG. 7, and in which device 10b is placed distal of device 10a. Device 10a creates a "proximal" pouch in stomach 30 (upstream from device 10a). From this pouch, device 10a regulates the flow of food (at a given rate) into a "mid pouch" created in stomach 30 between device 10a and 10b. Food flow from the mid pouch is further regulated (to a given rate) by device 10b.

In embodiments like those shown in FIGS. 7 and 8, the pressure threshold at which each device 10a/10b moves from one state to a second state may be the same or different. For example, one device 10a/10b may move to a second state at a pressure threshold lower than that of the second device. As a specific illustration, in an embodiment like FIG. 7 it may be desirable for the device 10b placed around the stomach to change to a second state and allow increased flow into the distal portion of the stomach at a lower pressure threshold than the esophageal device 10a to prevent reflux of stomach content into the esophagus.

In certain situations it may be advantageous to provide devices like 10 with compliance (force required to expand the device) during diametrical expansion that is more refined than can be provided by magnetic elements alone. In the case of two magnets, the attraction force is highest when the two are in contact, and the force decreases exponentially as the distance between the magnets increases. In the case of elastic materials, the force typically increases linearly with displacement distance. By combining magnetic elements and elastic materials in a device in accordance with this invention, the compliance characteristic of the diameter expansion and auto-adjusting parameters of the device can be further refined to balance weight loss and patient comfort or achieve whatever other or additional objectives the device has in use.

Figure 9:
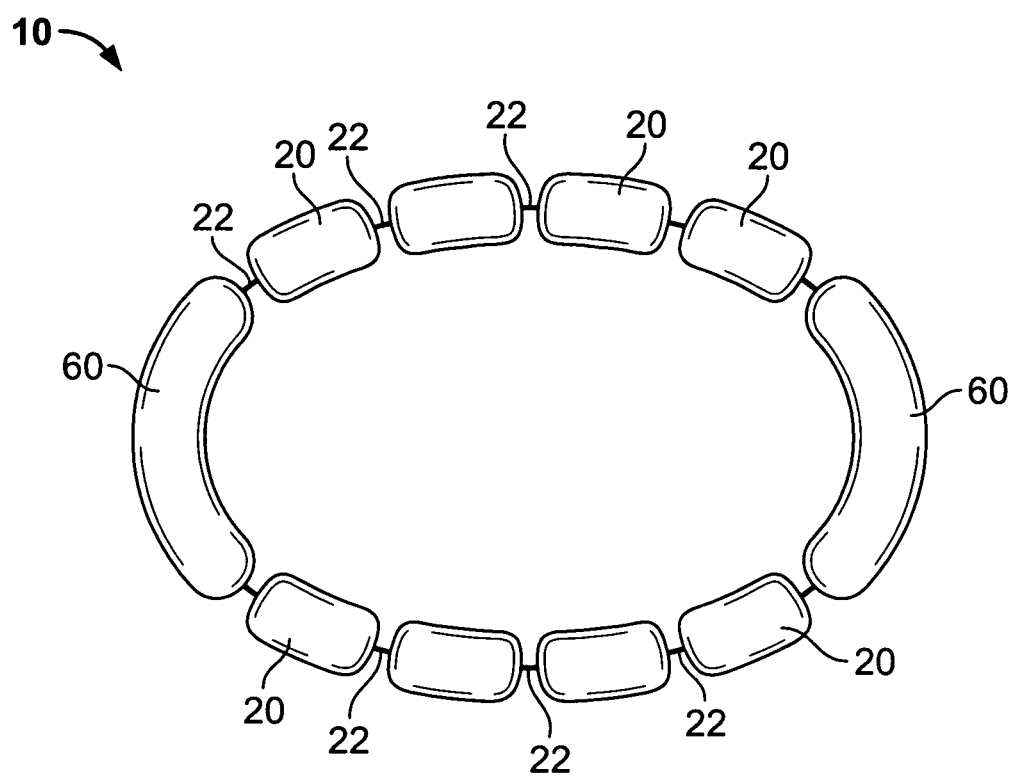
FIG. 9 is a simplified elevational view of another illustrative embodiment of apparatus in accordance with the invention.

An example of a device 10 having both magnetic elements and elastic elements as described in general terms in the preceding paragraph is shown in FIG. 9. As shown in FIG. 9, this device 10 includes magnetic elements 20 and elastic elements 60. Linking members 22 are provided between circumferentially adjacent ones of elements 20 and 60. One of the purposes of linking elements 22 is to maintain elements 20 and 60 in an annular array as shown in FIG. 9. Additionally, in the case of links 22 between circumferentially adjacent ones of magnetic elements 20, links 22 allow the adjacent elements 20 to move into contact with one another (in response to magnetic attraction) or to move away from one another to a predetermined maximum distance apart. This is the same function that is performed by links 22 between magnetic elements 20 in other embodiments of device 10 shown herein.

Figure 10:
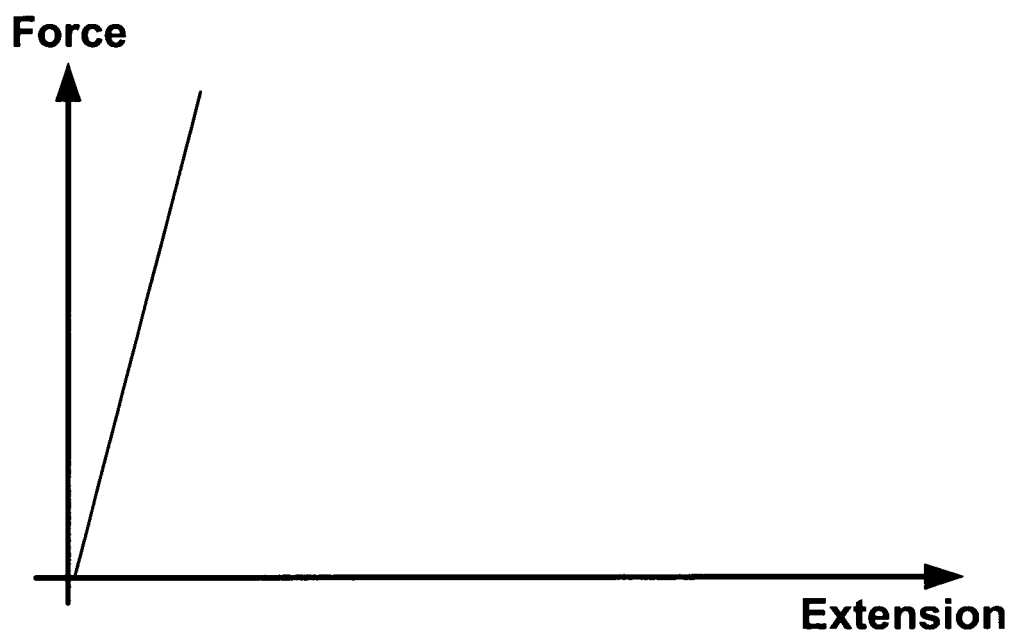
FIG. 10 is a simplified diagram that is useful in explaining certain possible aspects of the invention.
Figure 11:
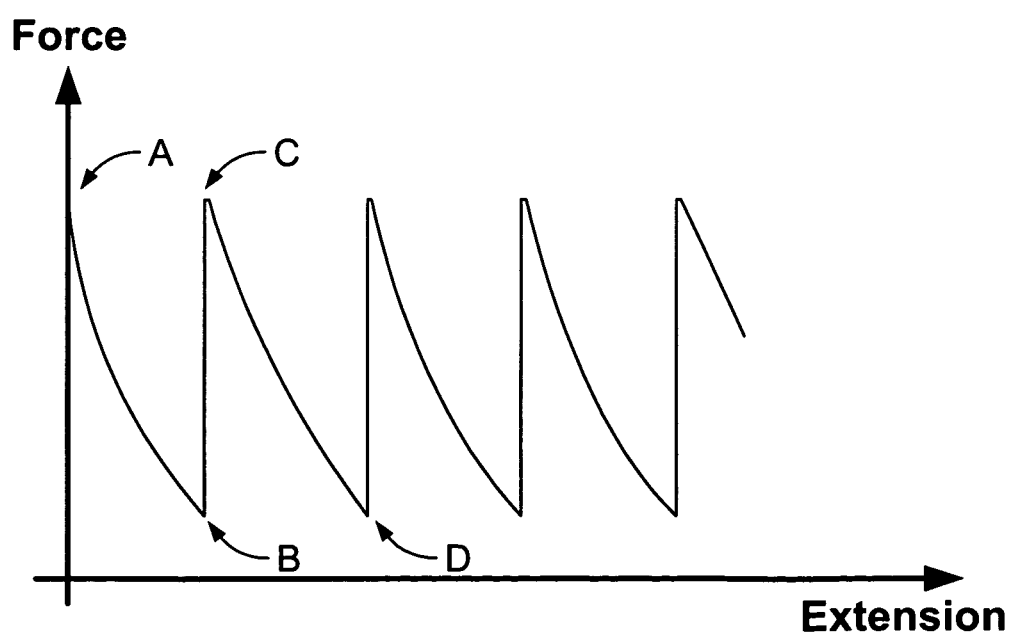
FIG. 11 is a simplified diagram that is useful in explaining certain other possible aspects of the invention.

In addition to the magnetic elements 20, the embodiment of device 10 that is shown in FIG. 9 includes two elastic elements 60 that interrupt the circumferentially extending series of magnetic elements at two locations around the circumference of the device 10. Each of elements 60 can elastically lengthen in the circumferential direction in response to pressure (force) that is trying to enlarge the circumference of device 10. When that pressure (force) diminishes, each of elements 60 attempts to elastically return to its original size. As noted earlier, this lengthening or shortening of members 60 is linear with the pressure or force acting to circumferentially enlarge device 10 (see FIG. 10, in which "force" represents device-enlarging force acting on a member 60, and "extension" represents circumferential elongation of that member). Circumferentially adjacent magnets 20 can also move apart in response to an increase in the above-mentioned pressure (force), and are mutually magnetically attracted back into contact with one another when that pressure (force) decreases. The behavior of a series of equally magnetically strong magnetic elements can be something like that shown in FIG. 11, where again force and extension have the same general meaning as above, except now applied to a series of circumferentially adjacent magnetic elements 20. In particular, as shown in FIG. 11, force acting to pull adjacent elements 20 apart can increase with no effect until point A is reached.

Then two (typically random) circumferentially adjacent elements 20 pull apart and may go to the maximum separation that the link 22 between them permits at point B. (In other words, the horizontal distance between points A and B (equal to the horizontal distance between points A and C) is the operative length of one typical link 22.) Force can then increase again with no effect until point C is reached, at which point two more adjacent elements 20 pull apart and may go to maximum spacing at point D. This pattern can repeat for as many instances as there are of circumferentially adjacent members 20.

Figure 12:
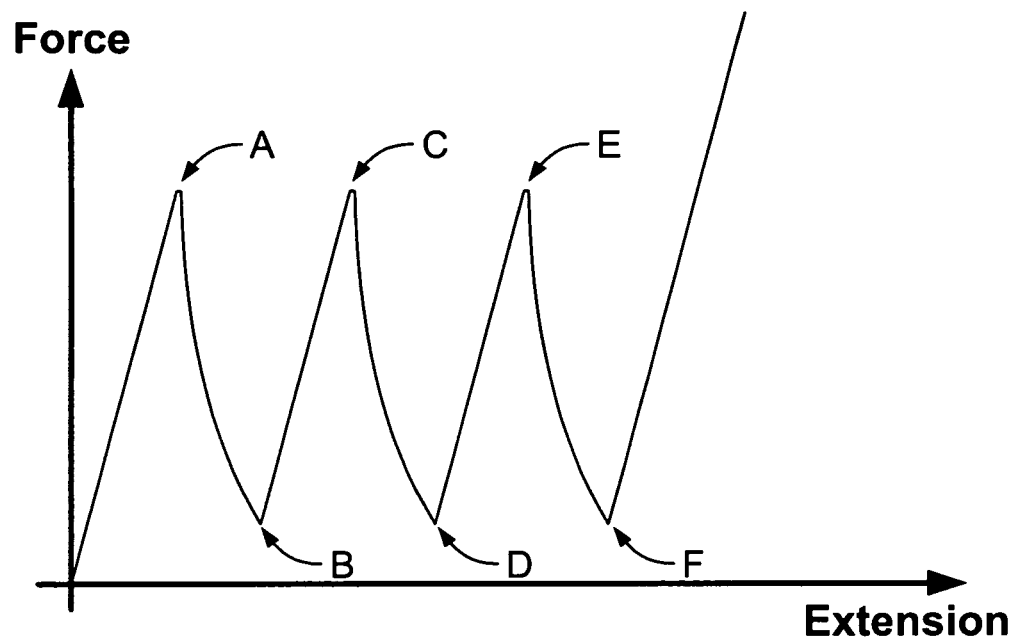
FIG. 12 is still another simplified diagram that is useful in explaining certain still other possible aspects of the invention.

FIG. 12 shows an example of behavior of a device 10 that includes both magnetic and elastic elements (e.g., as shown in FIG. 9). As compared to FIG. 11, the approach to point A in FIG. 12 is inclined (rather than straight up) due to the stretchability of elastic elements 60. At point A the first pair of circumferentially adjacent magnetic elements 20 begins to separate. At point B the first pair of magnetic elements 20 are as far apart as the link 22 between them will permit. If sufficient device-expanding force is still present, there is another incline upward from point B to point C. This incline is again due to the elasticity of elements 60. At point C the next pair of magnets 20 begins to separate, and the earlier-described process continues to repeat through points D, E, and F. Point E represents the beginning of separation of the last circumferentially adjacent pair of magnetic elements 20. When point F is reached, all of magnetic elements 20 are as far apart as the links between them will permit. To the right of point F, all further circumferential enlargement of device 10 is due solely to circumferential extension of elastic element(s) 60.

Figure 13:
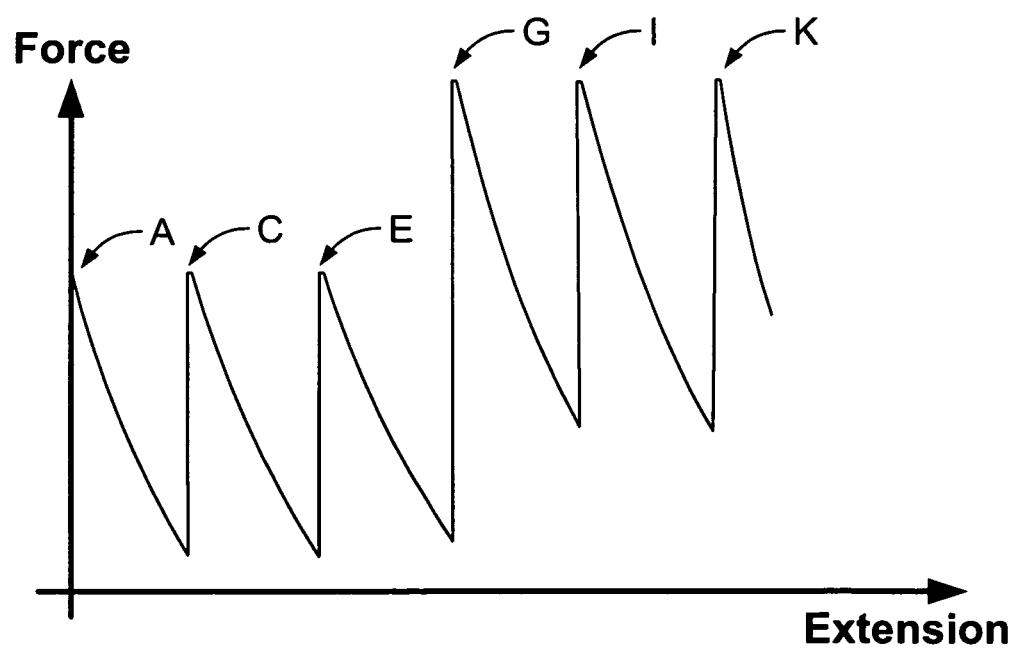
FIG. 13 is another simplified diagram that is useful in explaining certain other possible aspects of the invention.

FIG. 13 shows an example of behavior of a series of magnetic elements 20 in which some of those elements magnetically attract an adjacent element more strongly than other elements are attracted to one another. At point A the first relatively weakly attracting pair of elements 20 separate. At point C the next weakly attracting pair separates. At point E the final weakly attracting pair separates. Now significantly greater force must be reached (at point G) before the first more strongly attracted pair of elements 20 separates. That same higher force must be reached again (at points I and K) for the next and subsequent more strongly attracted pairs of elements 20 to separate. FIG. 13 shows how magnetic elements 20 of different magnetic strengths can be used to give device 10 a region (toward the left in FIG. 13) where relatively low force is required (e.g., as at A, C, E) to cause initial circumferential enlargement of the device, and another region (toward the right in FIG. 13) where relatively large force is required (e.g., as at G, I, K) to cause further circumferential enlargement of the device).

It will be apparent that elastic elements 60 can also be included in a device 10 having magnetic elements 20 that behave as shown in FIG. 13. If that is done, the result can be a modification of the behavior shown in FIG. 13 to convert the vertical lines in that FIG. to sloping lines (similar to what is shown in FIG. 12, and again concluding on the right with an all-elastic, upwardly inclined, final portion).

From the foregoing it will be seen that a device 10 in accordance with the invention can be designed to have different compliance of its diameter expansion and auto-adjusting parameters to balance such considerations as weight loss and patient comfort by using different materials (e.g., elastic and magnetic materials) in the device and/or by other means such as progressively stronger magnets at the various states of opening the device.

Figure 15:
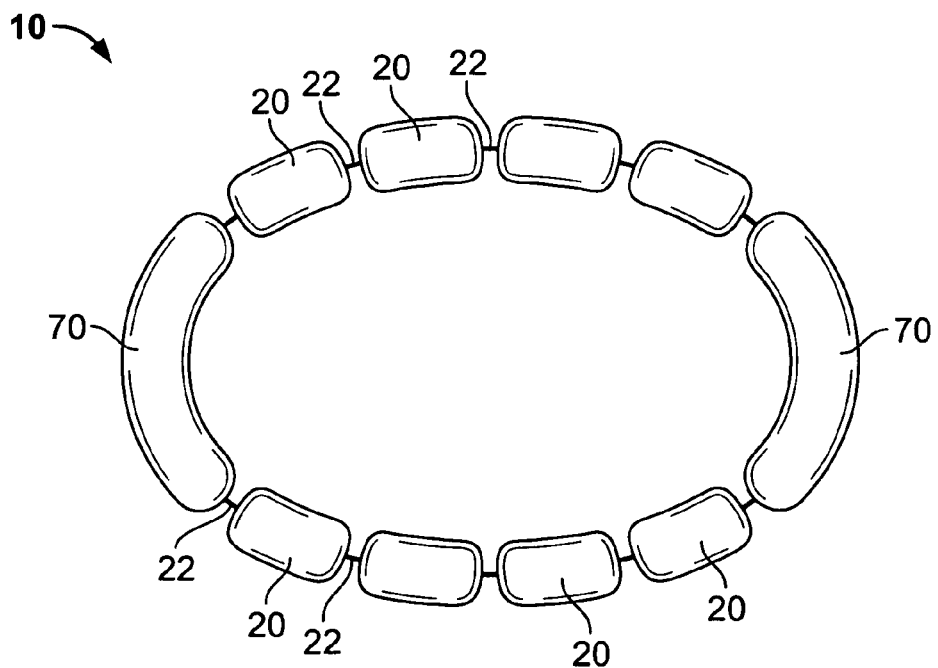
FIG. 15 is a simplified elevational view of yet another illustrative embodiment of apparatus in accordance with the invention.
Figure 16:
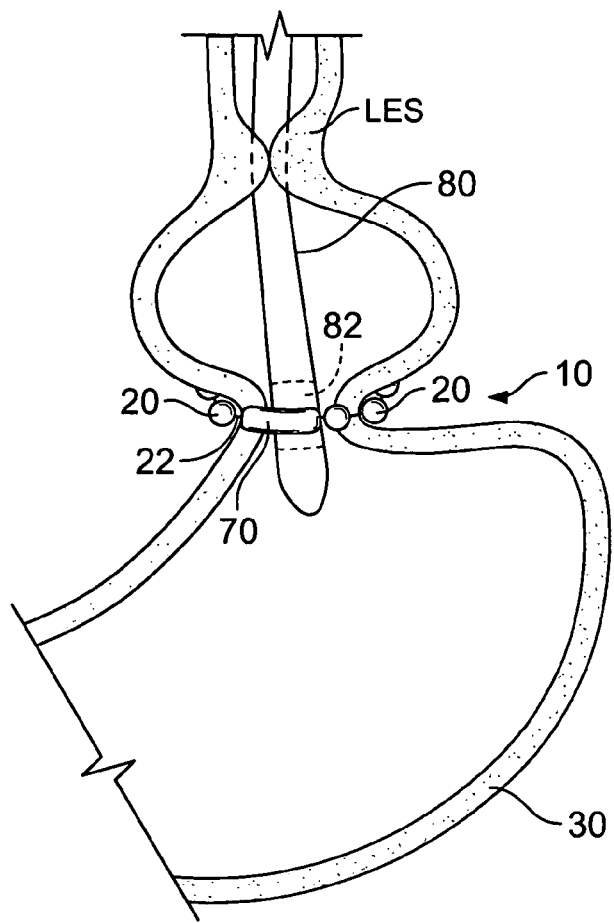
FIG. 16 is another view similar to FIG. 8 showing another illustrative embodiment of the invention.

Still another possibility that involves constructing device 10 with different materials is illustrated by FIG. 15. In this alternative, device 10 has an overall structure like that described above for the embodiment shown in FIG. 9, except that in FIG. 15 the elastic members 60 of the FIG. 9 embodiment are replaced by shape-memory polymer members 70. During the process of manufacturing this device 10, the alloy or polymer is set to a specific length and then stretched to a longer length and assembled in the device. The device is then implanted in a patient and provides automatic adjustment of its circumference by action of magnetic elements 20 as described for earlier embodiments. In the event the device is sized incorrectly or there is a desire for the device to provide a greater restriction to tissue structure 30, a catheter or other preferably non-invasive energy source may be introduced into the patient to apply energy to the shape-memory member(s) 70. For example, FIG. 16 shows insertion of a catheter-like instrument 80 into a patient via the patient's mouth. The distal end of catheter 80 passes through the lower esophageal sphincter LES into the portion of the patient's stomach that is encompassed by device 10. The distal portion of catheter 80 includes a source 82 of energy that shape-memory material 70 in device 10 is susceptible (responsive) to. When energy source 82 is adjacent to the members 70 of device 10, the energy source can be activated to emit energy that causes members 70 to return to their remembered shape. Because this remembered shape is shorter than the originally implanted shape, the at-rest circumference of device 10 is reduced. Catheter 80 is thereafter removed from the patient, and device 10 subsequently operates with a starting (at-rest) circumference that is smaller than the device had when it was first implanted in the patient.

It may be possible to apply the technique described in the preceding paragraph more than once. For example, only enough energy may be initially applied from source 82 to cause elements 70 to return part way to their remembered shape. If that shape change is not sufficient to produce the desired result, catheter 80 may be inserted into the patient again and more energy may be applied to cause elements 70 to change shape still more.

A possible feature of devices 10 in accordance with the invention is that they can be designed to accommodate post-procedural swelling in the tissue structure encompassed by the device. For example, in a device 10 placed around a proximal portion of a patient's stomach 30, the first state of the device may be sized to create a stoma having a diameter of approximately 12 mm to control the rate of food passage through the stomach. The device 10 may be designed to self-regulate to a second larger state in response to edema-related pressure increases within the tissue due to injury and healing response. This may be desirable to prevent the swelling from decreasing the size of the stoma and interfering with the rate of passage of food through the stomach. When the swelling resolves and the edema-related pressure within the tissue decreases below a prescribed threshold, the device self-regulates back to the first state to control the rate of food passage through the stomach.

Figure 17:
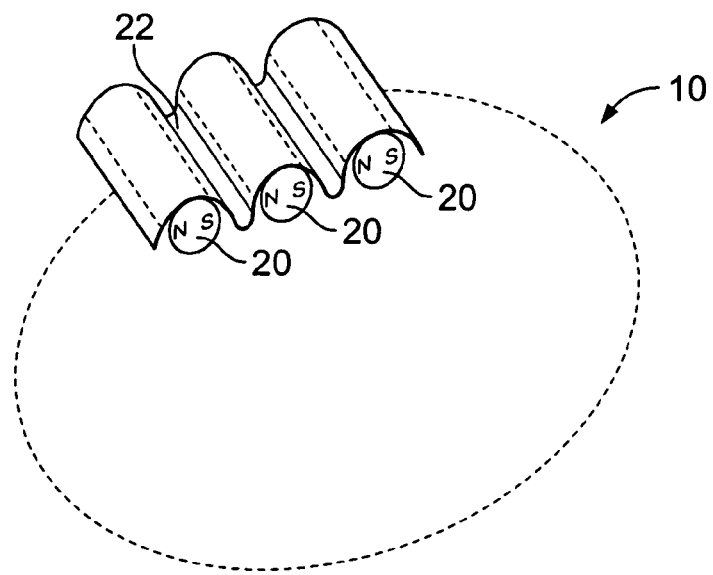
FIG. 17 is a simplified, partial, perspective or isometric view of another illustrative embodiment of apparatus in accordance with the invention.
Figure 18:
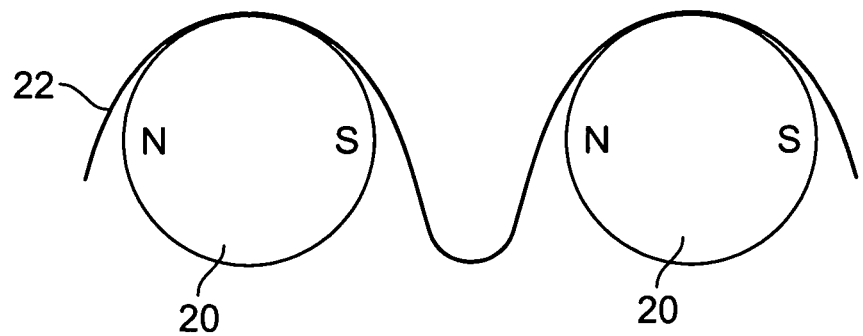
FIG. 18 is a simplified, partial, elevational view of apparatus like that shown in FIG. 17 in accordance with the invention.

FIGS. 17 and 18 show another illustrative embodiment of how a device 10 in accordance with the invention can be constructed. In this embodiment each magnetic element 20 is a rod of magnetic material having a longitudinal axis that is substantially parallel to an axis about which device 10 is annular. Each rod 20 is attached along one of its sides to a sheet 22 of fabric or other similarly flexible, web-like material. When sheet 22 is stretched out, rods 20 are spaced from one another, side by side along the sheet. When such stretching of the sheet is relaxed, rods 20 magnetically attract one another and create slack sheet material between them as they come together. FIGS. 17 and 18 show some such slack sheet 22 material between each circumferentially adjacent pair of rods 20. Each rod 20 is magnetized so that it has one magnetic pole (e.g., N or North) along one side of its length, and the opposite magnetic pole (e.g., S or South) along the other side of its length. Thus each rod 20 magnetically attracts the adjacent rods 20 along the length of the rods. Sheet 22 keeps rods 20 in an annular array, and also limits the amount by which the rods 20 can move apart. Sheet 22 is thus functionally related to links 22 in other, earlier-described embodiments.

Figure 19:
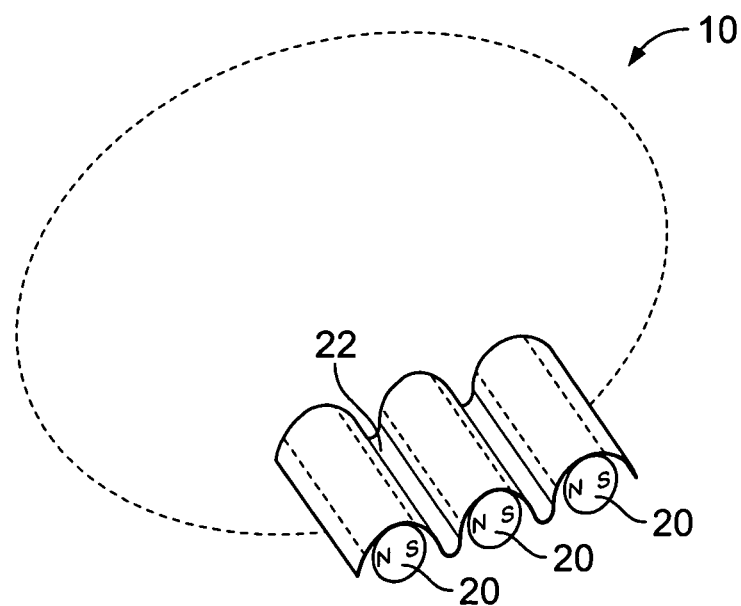
FIG. 19 is similar to FIG. 17 for another illustrative embodiment of the invention.

Whereas FIG. 17 suggests that sheet 22 is outside of magnets 20 when device 10 is implanted in a patient as an annular array, it may be preferable for sheet 22 to be inside the array of magnets in such an implant (see FIG. 19). In this way sheet 22 can additionally provide buffering between magnets 20 and the tissue 30 around which device 10 is implanted. This can help reduce possible erosion of the tissue by the presence and/or motion of device 10.

Figure 20:
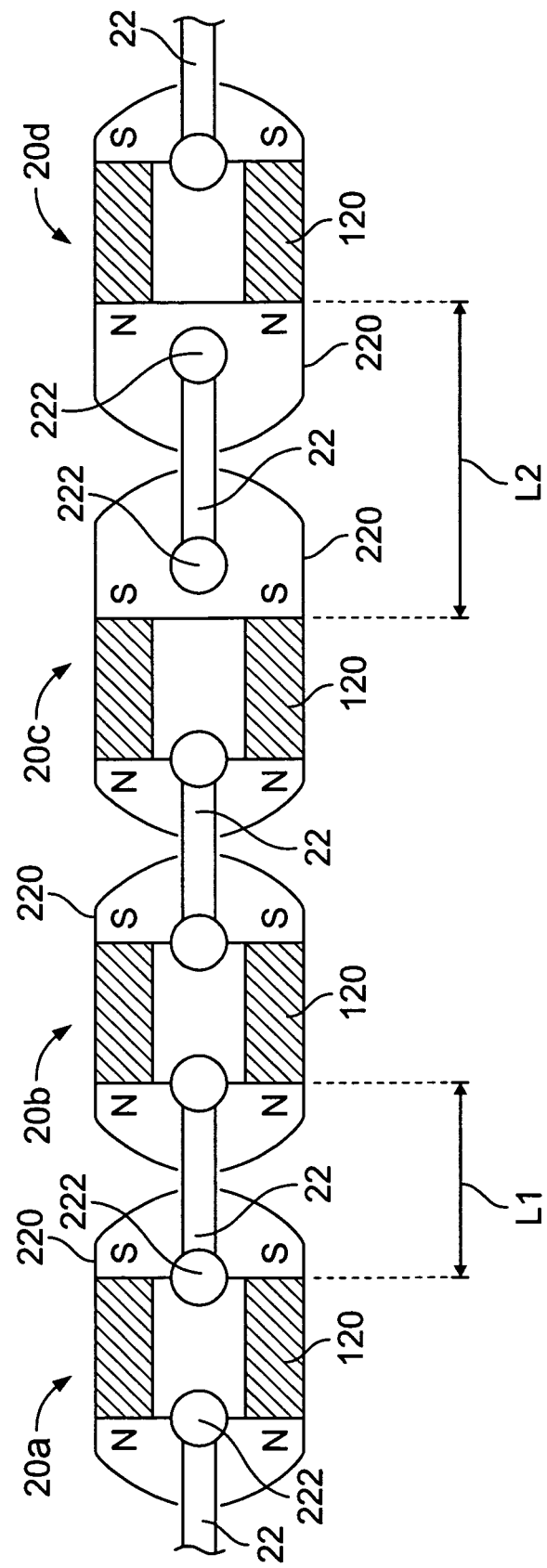
FIG. 20 is a simplified, partial, sectional view of an illustrative embodiment of apparatus in accordance with the invention.

FIG. 20 shows an example of how a device 10 can be constructed so that different magnetic elements 20 have different amounts of magnetic attraction to other circumferentially adjacent magnetic elements 20. In FIG. 20 each magnetic element 20 includes permanent magnet 120 inside a housing or enclosure 220. For example, each of magnets 120 may be a ring magnet. The polarization of each magnet 120 is indicated by the letters N and S adjacent each magnet. All magnets 120 can have the same size and magnetic strength. In each of magnetic elements 20a and 20b the magnet 120 is centrally located in the associated housing 220 along the axial length (left to right) of the housing. Magnetic elements 20c and 20d, however, have axially longer housings 220. In element 20c the magnet 120 is located asymmetrically toward the left in the housing 220, and in element 20d the magnet 120 is located asymmetrically toward the right in the housing 220. Dimension L1 is the approximate at-rest distance between the magnets 120 in elements 20a and 20b. Dimension L2 is the approximate at-rest distance between the magnets 120 in elements 20c and 20d. It will be apparent that L2 is greater than L1. Accordingly, the maximum force of magnetic attraction between elements 20a and 20b (which maximum force occurs when these elements are closest together or "at rest" as shown in FIG. 20) is greater than the maximum force of magnetic attraction between elements 20c and 20d. FIG. 20 therefore shows an example of how the magnetic elements 20 in a device 10 can be constructed so that different circumferentially adjacent ones of those elements have different amounts of maximum magnetic force of attraction between them.

FIG. 20 also shows another example of how links 22 between circumferentially adjacent ones of magnetic elements 20 can be constructed. In this embodiment each link 22 is shaped like a barbell. The enlarged head 222 on each end of each link 22 is inside the housing 220 of a respective one of the two circumferentially adjacent magnetic elements 20 that are connected by that link. The shaft between the heads 222 of a link is able to slide into and out of the housings 220 of the elements 20 joined by that link, but the heads 222 are not able to come out of those housings. The length of the shaft of each link 22 is great enough to allow the elements 20 joined by that link to move apart from the at-rest condition of those elements. However, such movement of elements 20 apart stops when the heads 222 on the link 22 joining those elements reach and contact the inner surface of the housings 220 of those elements.

Figure 14:
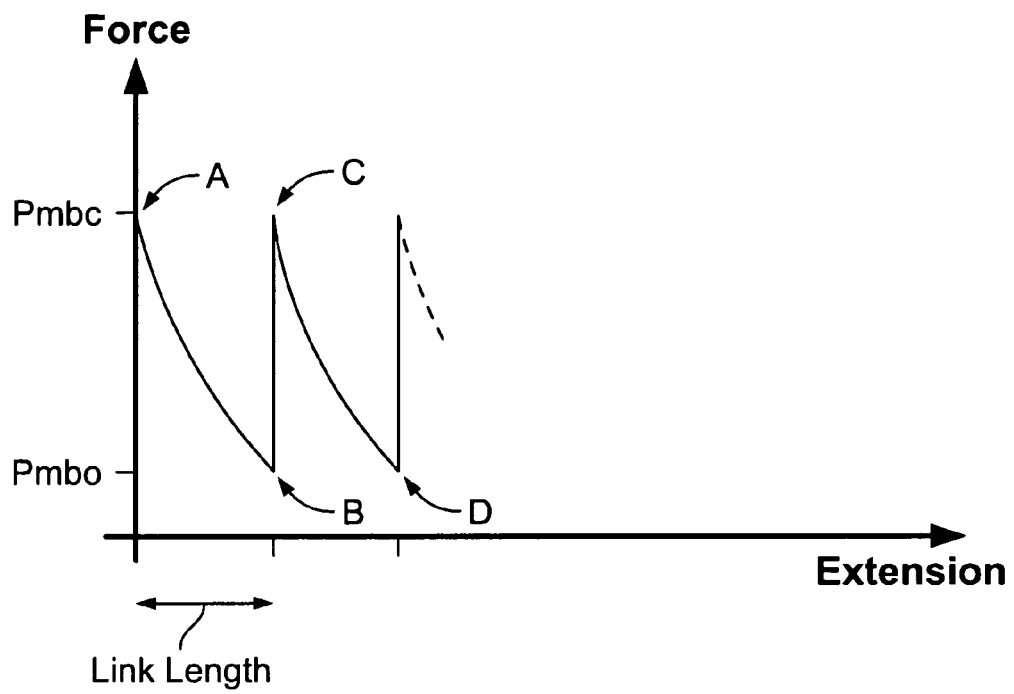
FIG. 14 is yet another simplified diagram that is useful in explaining certain further possible aspects of the invention.

Recapitulating and in some respects extending the foregoing, in an illustrative embodiment of the invention an array of magnetic beads 20 is placed circumferentially around the upper or proximal stomach 30 to create a small stomach pouch and an outflow restriction (stoma) to food matter as shown, for example, in FIG. 4. The magnetic beads 20 are connected (e.g., via links 22) in a way that limits the distance that circumferentially adjacent beads can move apart. Connections 22 also maintain a circumferential geometry to the array of beads 20. The composition and mass of adjacent magnets 20 and the space between them determines a specific pressure or force required to separate them when closed (Pmbc) (see FIG. 14, which is similar to FIG. 11, but with some additional parameters shown for purposes of the discussion in this and subsequent paragraphs). The connection means 22 limits the magnitude of the distance between beads. This maximum separation (link length in FIG. 14) determines a second magnetic force or minimum force that acts to restore the beads to their closed configuration (Pmbo). As food is swallowed, it enters the stomach. The magnetic band (MB) 10 restricts the food from entering the larger stomach via pressure Pmb from magnetic attraction of the beads 20. Food continues to fill the pouch bounded proximally by the lower esophageal sphincter (LES) and distally by the self-adjusting band 10.

Once the pressure of the filled pouch (Psf) exceeds the magnetic resistance of the magnetic band 10 (Pmbc), the beads 20 of the band begin to actuate. Once the beads actuate, they separate in distance and the exit orifice created by the magnetic band 10 increases. This allows food to pass through band 10 and enter the distal stomach. This continues until Pmbo is greater than Psf, at which time the magnetic band 10 will close again until further food increases the volume and pressure of the pouch.

If Psf is greater than Ples (the closing pressure of the lower esophageal sphincter), then food may reflux into the esophagus rather than actuate the magnetic band 10 and enter into the lower stomach. Thus another illustrative embodiment (e.g., as shown in FIG. 7) can include a magnetic band 10a placed at the LES region of the esophagus, and another magnetic band 10b placed around the proximal stomach. In this case the formed pouch is defined by a magnetic band 10 on both the proximal food entrance and the distal food exit. The actuation pressure Pmbc of the first (proximal) magnetic band 10a may be greater than the actuation pressure of the distal or second magnetic band 10b.

Figure 5:
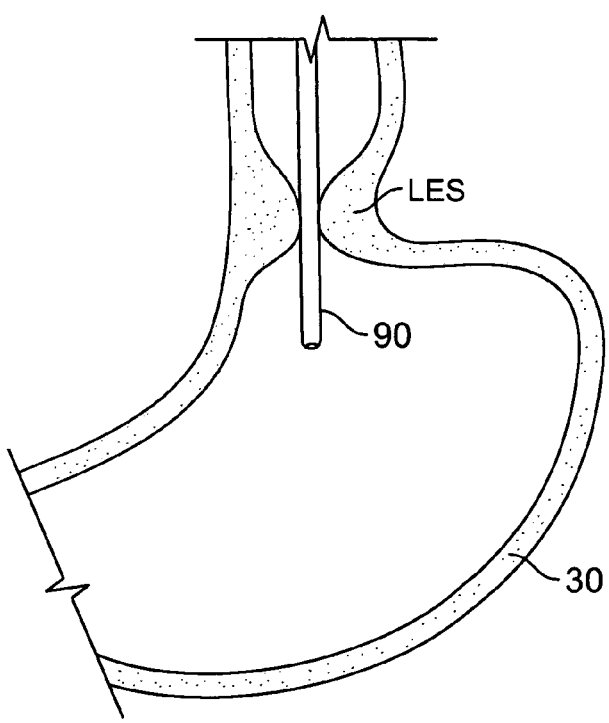
FIG. 5 is similar to FIG. 3, with insertion of another illustrative object into the anatomy in accordance with certain possible aspects of the invention.
Figure 6:
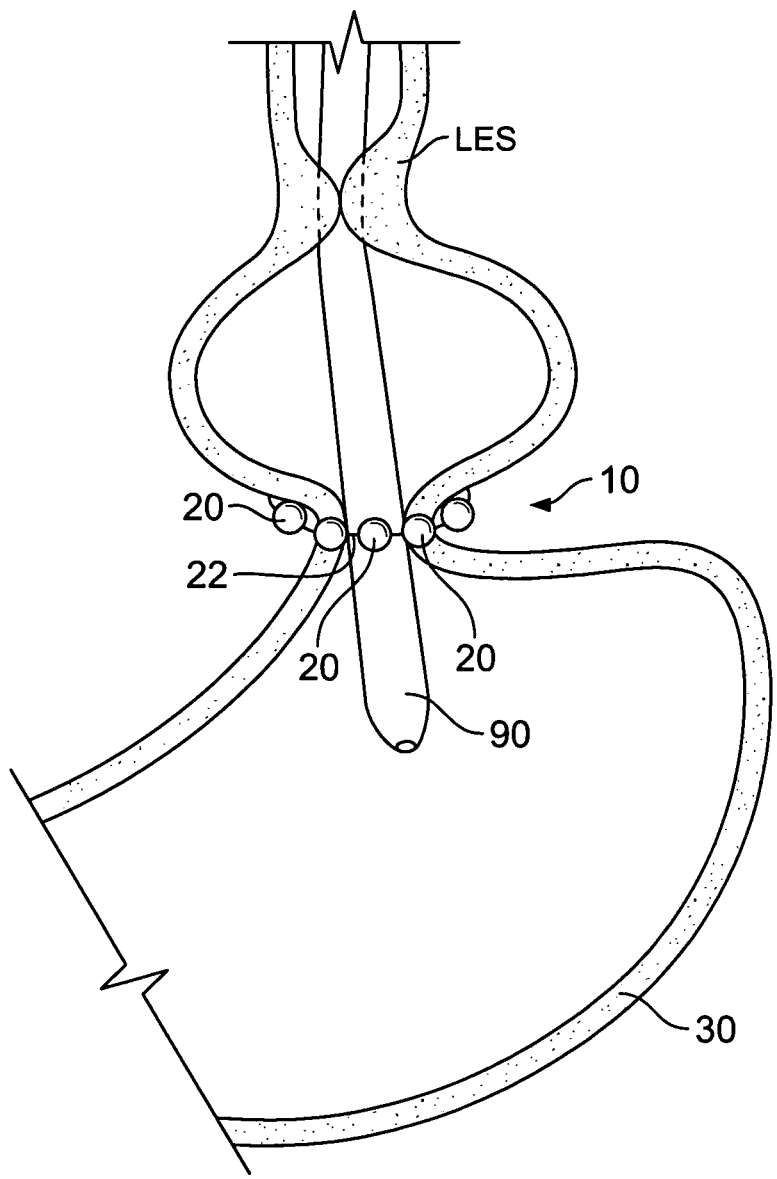
FIG. 6 is another view similar to FIG. 5 showing a later stage in use of what is shown in FIG. 5 in accordance with the invention.

As shown in FIG. 5, a dilator or solid cylindrical object 90 may be placed via the patient's mouth, through the esophagus, and into the stomach to the location at which device 10 is to be implanted around the stomach. Device 10 is then implanted so as to snug the encompassed tissue down around (i.e., into contact with the outer cylindrical surface of) object 90 (see FIG. 6). Object 90 is sized to create a more consistent stoma diameter when device 10 is thus implanted. Object 90 is then withdrawn from the patient through the patient's mouth. In some embodiments, when the magnetic band 10 is fully closed, it is desired for that band to keep the stoma to a specific diameter that is greater than zero. The technique illustrated by FIGS. 5 and 6 can help to achieve this, e.g., by giving object 90 the immediately above-mentioned specific diameter. In another embodiment the dilator or similar object 90 can be used to size the magnetic band 10 to define the maximum diameter the stoma can become (i.e., all magnetic beads 20 fully separated by as much as their links 22 will allow).

With reference to what is described in the immediately preceding paragraph as "a specific diameter that is greater than zero," it will be apparent that this defined opening can be used to regulate a flow rate through the stoma and into the stomach. When pressure in the pouch is greater than Pmbc (and also less than Ples), the magnetic band 10 can open to allow this flow rate to further increase. As the flow continues, the pressure in the pouch will drop and the magnetic band will close down again to restrict the opening.

International publication No. WO 2006/020382 shows some examples of how the magnetic bands 10 that are used in accordance with this invention can be constructed. (WO 2006/020382 is hereby incorporated by reference herein in its entirety.) For example, these magnetic bands can be made up of a plurality of magnetic beads 20 or the like in an annular array. Each bead 20 in the array is oriented so that it magnetically attracts the two beads that are immediately adjacent to it in the array (i.e., the two beads that are on respective opposite sides of the first-mentioned bead in the array). Between each annularly adjacent pair of beads 20 in the array there is a linking member 22. Each linking member 22 allows the two beads that it links to move away from one another along the length of the linking member. However, the amount that two beads 20 can thus move away from one another is limited by the link member 22. The link members 22 also function to maintain the arrangement of the beads in the form of an annular array at all times. The circumference of the array 10 is variable from a smallest size when each bead 20 is in contact with its two immediately adjacent neighboring beads, to a largest size when each bead has moved as far away from its neighboring beads as the link members 22 permit. Any circumferential size between these smallest and largest sizes can also occur. Magnetic attraction between the beads 20 is always urging the array toward its smallest size. The magnetic strength of the beads 20 determines how strongly they resist moving apart. Even in its smallest size, the array preferably leaves open a lumen of non-zero area through the array.

Even when all the beads 20 are of equal magnetic strength, the array 10 can exhibit a kind of stepwise opening and closing behavior. During opening, for example, what typically happens is that two of the beads 20 (due to variability of manufacturing processes) begin to move apart, and continue to do so until the maximum link length between those beads is reached. If a still larger array size is needed, then two more beads 20 begin to move apart until they reach the maximum link length between them. This stepwise process continues as long as necessary, coming to a final stop when all of the beads have moved away from their neighbors by the maximum amount permitted by the link members 22. This stepwise process may reverse itself as the array 10 closes down again.

The stepwise opening and closing of the array 10 described in the preceding paragraph can result in behavior somewhat like that shown in FIG. 1 (array diameter plotted on vertical axis; opening pressure plotted on horizontal axis). If it is desired to more strongly and positively effect such multi-step behavior, the array 10 can be made with beads 20 that have several different (i.e., graduated) magnetic strengths, and therefore with different amounts of magnetic attraction between adjacent beads. Beads 20 that are less strongly attracted to one another will separate first (in response to relatively low pressure increases). Beads 20 that are more strongly attracted to one another will not separate in response to such relatively low pressure increase; but if pressure continues to rise sufficiently, these more strongly attracted beads will also begin to separate following maximum link separation from the less strongly attracted beads. From this it will be seen that very definite steps can be engineered into the array 10, if desired, in order to ensure stepwise behavior like that shown in FIG. 1.

It will be understood that the foregoing is only illustrative of the principles of the invention, and that various modifications can be made by those skilled in the art without departing from the scope and spirit of the invention. For example, the numbers, sizes, and shapes of various components shown herein are only some illustrations of what can be done, and many variations of these parameters are possible. It will also be appreciated that while some aspects of what is shown and described herein may be of primary interest in connection with gastric banding, other aspects are of more general interest and applicability. For example, devices 10 that include both magnetic and elastic components (e.g., as shown in FIG. 9) can be used anywhere in a patient's body where such a device can be beneficially applied to a tissue structure. The same is true for devices that include both magnetic and shape-memory components (e.g., as shown in FIG. 15).

The invention claimed is:

1. An implant for use in a patient's body comprising:
a plurality of magnetic elements; and
means for maintaining the magnetic elements in a serial array that can be disposed to extend in a circumferential direction around a body tissue structure in the patient, each of the magnetic elements magnetically attracting at least one other circumferentially adjacent one of the magnetic elements and being able to move in the circumferential direction toward and away from that other circumferentially adjacent magnetic element, a maximum force of magnetic attraction, over a given separation distance, between a first pair of circumferentially adjacent ones of the magnetic elements that are able to move toward and away from one another being greater than a maximum force of magnetic attraction, over the given separation distance, between a second pair of circumferentially adjacent ones of the magnetic elements that are able to move toward and away from one another, the means for maintaining including respective links defining a maximum separation distance between the magnetic elements in each respective first pair, and between the magnetic elements in each respective second pair.

2. The implant defined in claim 1 wherein the means for maintaining permits circumferentially adjacent ones of the magnetic elements to move into contact with one another.

3. The implant defined in claim 1 wherein the implant is adapted for implanting around the patient's stomach, and wherein the maximum force of magnetic attraction between the first pair is selected to be overcome by gastric pressure proximal to the implant that is greater than gastric pressure needed to overcome the maximum force of magnetic attraction between the second pair.

4. A method for treating obesity comprising:
disposing a band around the outside of the stomach to segment the stomach into more than one cavity, the band being configured to leave a lumen of restricted size in the stomach between the cavities, and the band including a plurality of magnetic elements, each of the magnetic elements magnetically attracting at least one other circumferentially adjacent one of the magnetic elements and being able to move away from or toward one another to dynamically adjust the size of the lumen in response to a physical parameter, a maximum force of magnetic attraction, over a given separation distance, between a first pair of circumferentially adjacent ones of the magnetic elements that are able to move toward and away from one another being greater than a maximum force of magnetic attraction, over the given separation distance, between a second pair of circumferentially adjacent ones of the magnetic elements that are able to move toward and away from one another.

5. The method of claim 4 wherein the physical parameter is gastric pressure.

6. The method of claim 4 wherein the lumen of restricted size partially blocks passage of food until a physical parameter threshold is reached and the band dynamically adjusts to increase the size of the lumen.

\* \* \* \* \*